United States Patent [19]

Thibault et al.

[11] Patent Number: 5,607,400
[45] Date of Patent: Mar. 4, 1997

[54] PRE-FILLABLE SYRINGE AND STOPPER ASSEMBLY THEREFOR

[75] Inventors: Jean-Claude Thibault, Saint-Egreve; Jean-Pierre Grimard, Vif; Catherine F. Faure, Grenoble, all of France

[73] Assignee: Becton, Dickinson and Company, Franklin Lakes, N.J.

[21] Appl. No.: 445,130

[22] Filed: May 19, 1995

[51] Int. Cl.⁶ ................................................. A61M 5/315
[52] U.S. Cl. ............................................ 604/230; 604/218
[58] Field of Search .................................... 604/230, 228, 604/220, 218, 187, 89–91, 191

[56] References Cited

U.S. PATENT DOCUMENTS

| 4,874,381 | 10/1989 | Vetter ........................... 604/191 |
| 5,009,646 | 4/1991 | Sudo et al. ..................... 604/230 |
| 5,290,228 | 3/1994 | Uemura et al. ............... 604/230 X |

FOREIGN PATENT DOCUMENTS

| 338671 | 8/1981 | European Pat. Off. . |
| 33730 | 3/1988 | Japan . |
| 5057018 | 3/1993 | Japan ........................... 604/230 |
| 5131029 | 5/1993 | Japan ........................... 604/230 |

Primary Examiner—John D. Yasko
Attorney, Agent, or Firm—Vincent A. Castiglione

[57] ABSTRACT

A pre-fillable hypodermic syringe is provided. The hypodermic syringe includes a syringe barrel having opposed proximal and distal ends and a drug-receiving chamber therebetween. The distal end of the syringe receives a needle cannula that is sealingly and protectively covered by a cap. The proximal end of the syringe is sealed by a stopper assembly. The stopper assembly includes a distal stopper that is positioned adjacent the drug pre-filled into the syringe barrel. The distal stopper is formed to exhibit acceptably low sliding forces without the presence of lubricants deleterious to the drug. The stopper assembly further includes a proximal stopper formed from a material that exhibits acceptable microbiological sealing. Because the proximal stopper is separated from the drug by the distal stopper the proximal stopper may be treated with any convenient lubricant, such as silicone oil. The distal stopper functions as a barrier between the drug and the lubricant such as silicone oil that is on or near the proximal stopper. The proximal stopper, on the other hand, provides the required microbiological sealing.

25 Claims, 4 Drawing Sheets

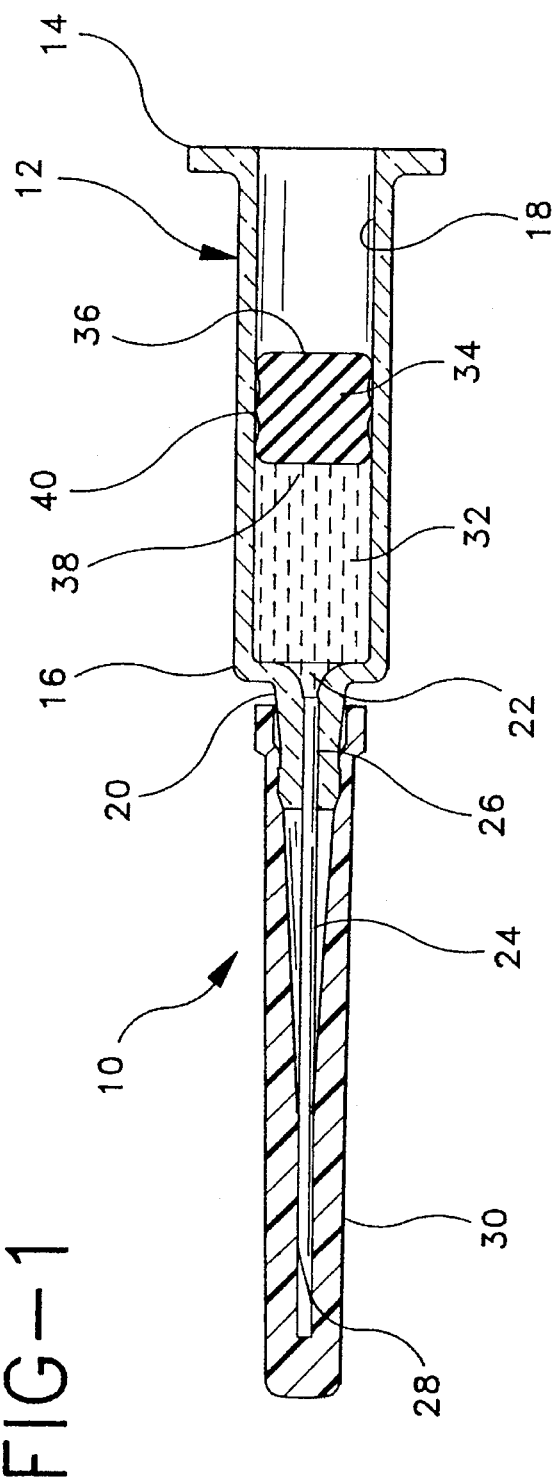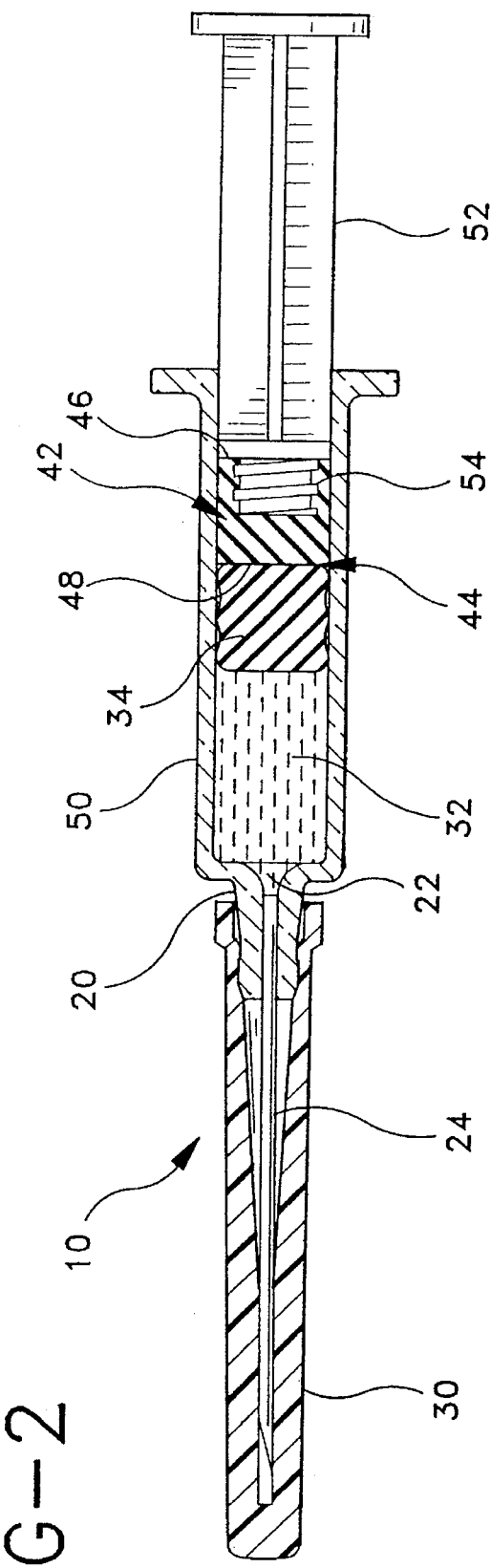

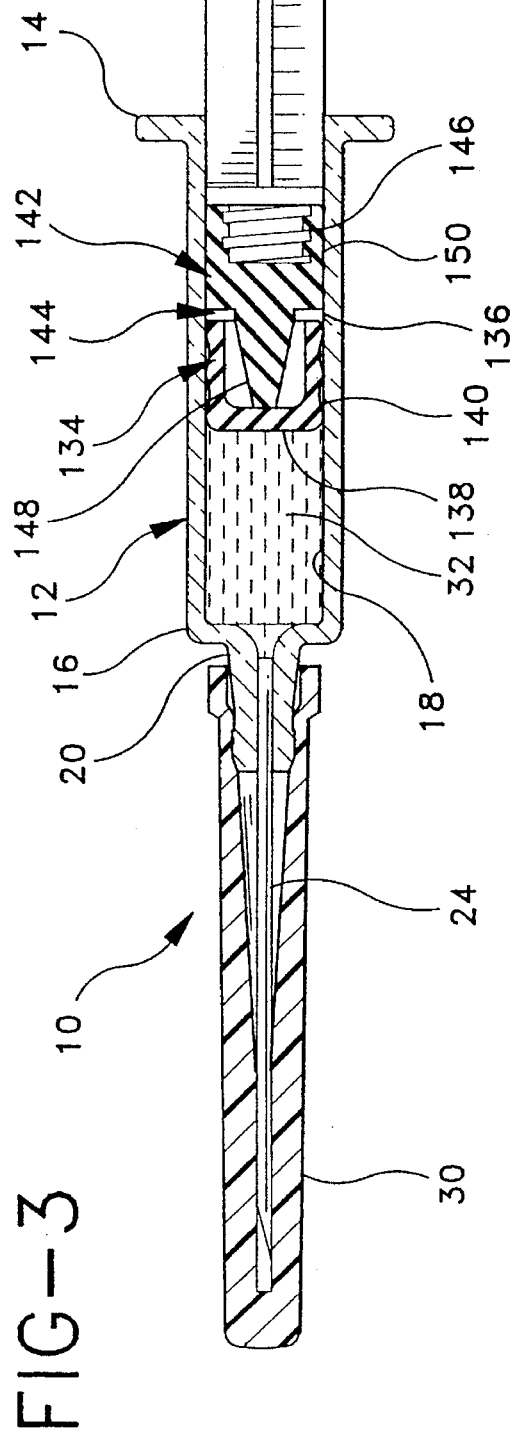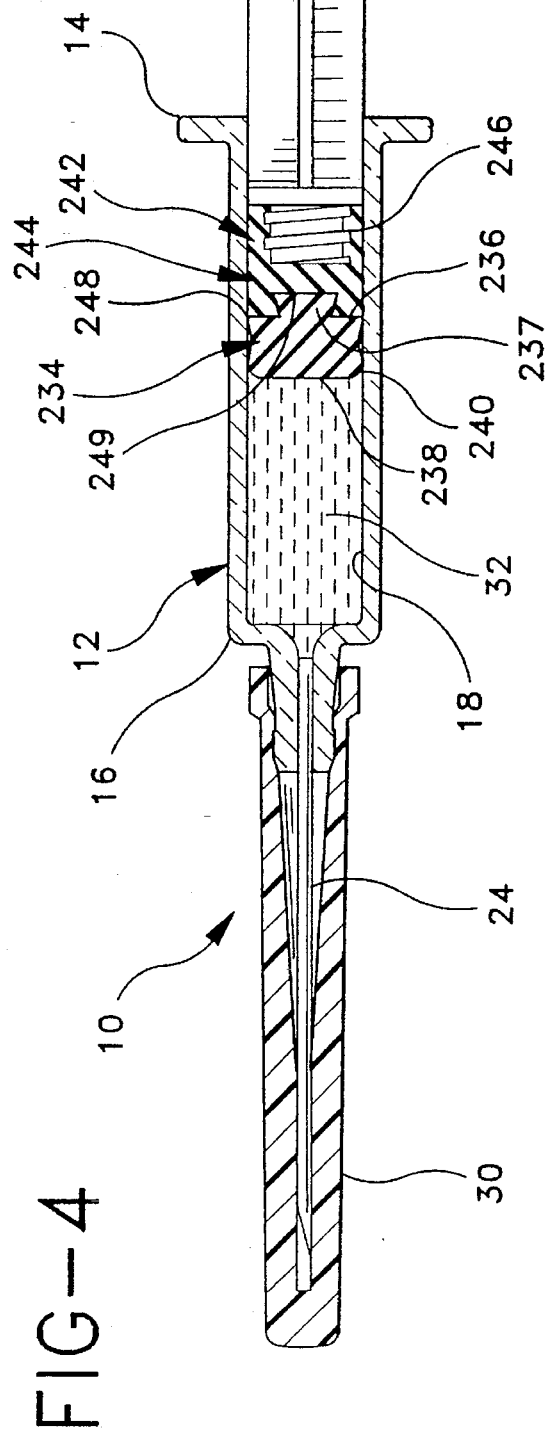

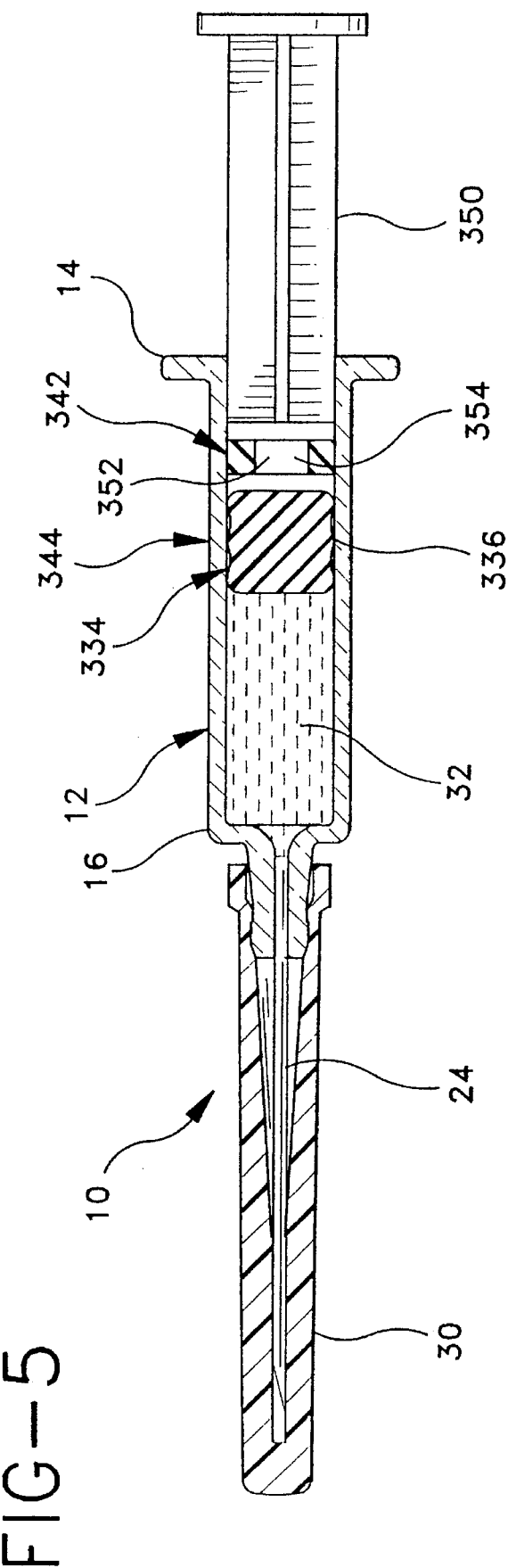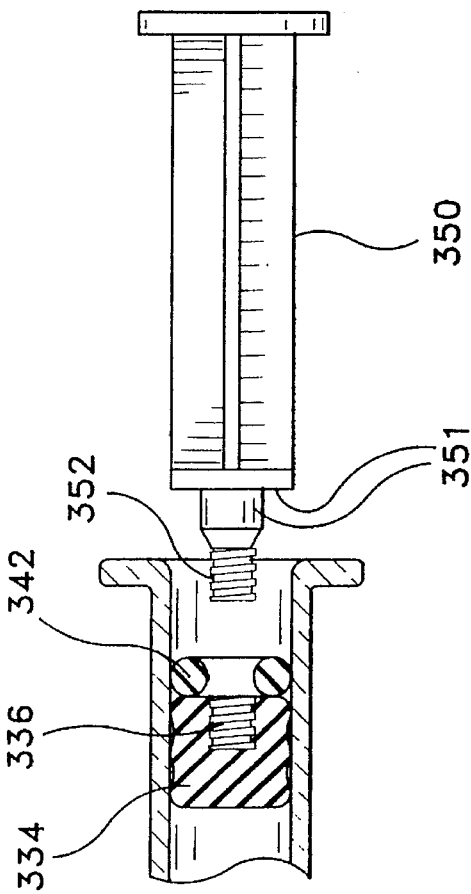

PRE-FILLABLE SYRINGE AND STOPPER ASSEMBLY THEREFOR

BACKGROUND OF THE INVENTION

1. Field of the Invention

The subject invention relates generally to pre-filled syringes and to stoppers for such syringes.

2. Description of the Prior Art

The prior art syringe includes an elongate barrel having opposed proximal and distal ends and a fluid receiving chamber therebetween. The distal end of the prior art syringe barrel includes a small diameter passage that communicates with the fluid receiving chamber and with the lumen of a piercing element, such as a pointed needle cannula or a blunt-ended cannula, that is mounted to the syringe barrel. The proximal end of the prior art syringe barrel is generally open for slidably receiving a plunger. The plunger typically includes a distal end configured to mate with a rubber stopper that is in sliding fluid-tight engagement with the inner wall of the chamber. A distal force on the plunger and stopper urges fluid in the chamber through the passage of the syringe barrel and through the needle that communicates with the passage. A proximal force on the plunger and stopper urges fluid proximally through the passage and into the chamber of the prior art syringe barrel.

Many prior art syringes remain empty until shortly prior to use. These prior art syringes are used by placing the needle in communication with a drug and moving the plunger proximally to aspirate the drug into the chamber of the syringe barrel. The drug may then be administered by placing the distal end of the needle in communication with the patient or with an IV set or other device, and urging the plunger distally to expel the drug from the syringe barrel.

The filling of a syringe immediately prior to use requires the time, skill and attention of the health care worker. Health care workers often work under emergency circumstances with numerous simultaneous demands for their time, skill and attention. At the very least, filling a hypodermic syringe immediately prior to use creates an inconvenience for the healthcare worker, and can create the potential for improper selection and dosing of a drug.

Frictional forces between the rubber stopper and the syringe barrel can be significant and can impede a slow, predictable and accurate flow of drug into or out of the syringe barrel. As a result, most prior art syringes employ a low friction material or lubricant, oftentimes a silicone-based lubricant such as a silicone oil, to facilitate the sliding movement of the stopper in the syringe barrel. The lubricant may be applied as a coating over the stopper or may be applied to the walls of the chamber in the syringe barrel.

To avoid problems associated with filling the syringe immediately prior to use, pharmaceutical companies sometimes prefer to ship medicaments in pre-filled syringes. The pre-filled syringes are appropriately sealed, clearly labeled, and shipped to health care facilities in properly measured doses. Thus, a healthcare worker avoids many of the steps associated with point of injection syringe filling. The healthcare worker merely accesses an appropriate pre-filled syringe and injects the required dose without the above described inconveniences associated with filling the syringe immediately prior to use. Pre-filled syringes are widely used for a broad range of drugs that have an acceptably long shelf life. However, owing to certain factors such as the duration of storage which pre-filled syringes might sustain, many drugs that are otherwise appropriate for pre-filled syringes may sometimes be incompatible with the lubricant or low friction material, such as silicone oil, used to facilitate the sliding movement of the stopper through the syringe barrel. For instance, protein based drugs or drugs based on biogenetic technology may sometimes display compatibility difficulties respective of the silicone employed as a syringe lubricant.

The prior art includes stoppers with laminated films or coatings to reduce friction without using silicone-based lubricants. For example, U.S. Pat. No. 5,009,646 teaches laminating a rubber elastic body with a tetrafluoroethylene resin, an ethylenetetrafluoroethylene resin or a UHMW polyethylene resin. These laminated stoppers may work well for syringes that are filled immediately prior to use. However, the laminated materials may tend to creep after placement in the syringe barrel. As a result, microchannels are opened that may permit the drug in the syringe barrel to communicate with ambient air. Thus, the adequacy and effectiveness of the drug can be compromised by using these prior art stoppers laminated with a non-silicone, low friction material.

In view of these problems, certain drugs that would otherwise be appropriate for pre-filled syringes must be filled immediately prior to use by the health care worker to avoid contaminating the drug, either because of the presence of lubricants or low friction materials such as silicone-based lubricants or contamination owing to unwanted communication with the ambient atmosphere.

SUMMARY OF THE INVENTION

The subject invention is directed to pre-filled syringes and, in particular, to stopper assemblies for pre-filled syringes. The syringe of the subject invention may include a syringe barrel with opposed proximal and distal ends and a fluid receiving chamber therebetween. The distal end of the syringe barrel may include a tip having a narrow fluid passage extending therethrough and communicating with the chamber of the syringe barrel. A piercing element such as a sharply pointed needle cannula or a blunt-ended cannula may be securely mounted to the tip such that the lumen through the piercing element communicates with the chamber of the syringe barrel. A protective cap may be sealingly engaged over the distal end of the syringe barrel. The protective cap functions to seal the distal end of the syringe barrel and to prevent accidental sticks with a piercing element that may be premounted thereon. The proximal end of the syringe barrel is open for slidably receiving a plunger and stopper assembly therein.

A specified dose of a selected drug is pre-filled into the syringe barrel for subsequent shipment to a medical facility and storage at the medical facility until the drug is needed. The end of the syringe barrel proximal of the drug dosage is protectively sealed by a sealing assembly in accordance with the present invention. The sealing assembly includes proximal and distal stoppers, which may be either spaced from one another, rest adjacent to one another or disposed interengaged with one another. The distal stopper may be formed from a resilient elastomeric material. To facilitate sliding, a low friction material may be laminated, sealed, glued, or otherwise disposed on the distal stopper. To avoid contaminating effects on the drug held in the syringe barrel, the low friction material should be substantially free of materials known to have adverse effects on drugs as hereinbefore recited, including silicone-based materials such as silicone oil. The material coated to the elastomeric material of the distal stopper is selected to exhibit acceptable sliding friction forces relative to the wall of the syringe barrel.

As noted above, silicone-free laminated or coated stoppers have been used in prior art syringes that are filled immediately prior to use, but have not been used for pre-filled syringes due to the tendency of the laminate or coating on the stopper to creep so as to permit microchannels to open. To offset this deficiency of the prior art, the proximal stopper is formed from a known elastomer that is appropriately lubricated with a lubricant. One example of such a lubricant is a silicone-based lubricant such as polydimethylsiloxane silicone oil. The proximal stopper functions as an absolute microbiological barrier that offsets the above noted sealing deficiencies of the distal barrier. Because the lubricating treatment of the proximal stopper is separated from the drug by the distal stopper, the proximal stopper can be treated with any convenient lubricating material, including silicone-based lubricants such as silicone oil, without undue risk of contamination to the drug held in the syringe barrel. Hence, contact between the drug and the lubricant is dramatically reduced if not eliminated so as to avoid the aforementioned problems.

The lubricating treatment of the proximal stopper can be achieved by applying the lubricant directly to the proximal stopper or by applying the lubricant to the inner walls of the syringe barrel after the distal stopper has been positioned.

BRIEF DESCRIPTION OF THE DRAWINGS

FIG. 1 is a longitudinal cross-sectional view of a pre-filled syringe with the distal stopper of the subject stopper assembly.

FIG. 2 is a longitudinal cross-sectional view similar to FIG. 1, but showing both the distal and proximal stoppers of the subject stopper assembly.

FIG. 3 is a cross-sectional view similar to FIG. 2, but showing a second embodiment of the stopper assembly.

FIG. 4 is a cross-sectional view similar to FIGS. 2 and 3, but showing a third embodiment of the stopper assembly.

FIG. 5 is a cross-sectional view similar to FIGS. 2–4, but showing a fourth embodiment of the stopper assembly.

FIG. 5a is an alternate configuration of the embodiment of FIG. 5.

DETAILED DESCRIPTION OF THE PREFERRED EMBODIMENT

Figure 6:
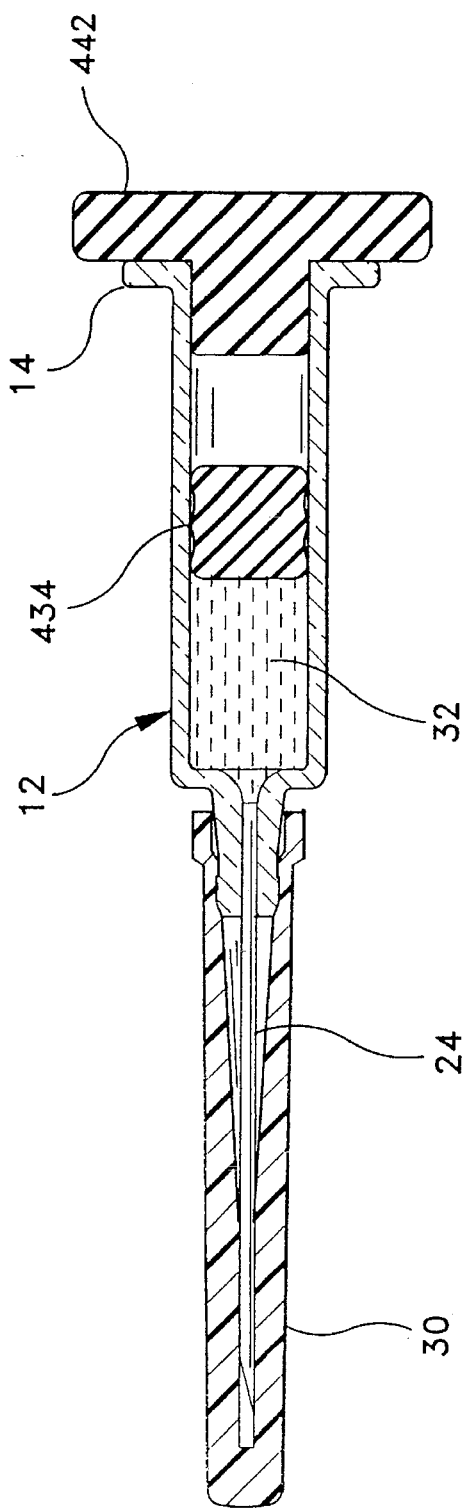
FIG. 6 is a cross-sectional view similar to FIGS. 2–5, but showing a fifth embodiment of a stopper assembly.

Turning now to the drawings, wherein like numerals denote like components, a hypodermic syringe in accordance with the subject invention is identified generally by the numeral 10 in FIGS. 1 and 2. Syringe 10 includes a generally cylindrical syringe barrel 12 having opposed proximal and distal ends 14 and 16 and a fluid receiving chamber 18 therebetween. The syringe barrel 12 can be formed of appropriate medical grade glasses, plastics, metals, or the like materials known to the skilled artisan. Distal end 16 of syringe barrel 12 includes an elongate tip 20 having a passage 22 extending therethrough and communicating with chamber 18 of syringe barrel 12.

A piercing element 24 is disposed at the distal end 16 of the syringe barrel 12. The piercing element 24 includes a proximal end 26 mated to the syringe barrel 14 and a distal end 28. As has been previously explained, it is within the purview of the present invention that the piercing element 24 can entail sharply pointed needle cannulae, or blunt-ended cannulae, such as those employed with the so-called needleless systems. For purposes of illustration but not of limitation, as herein shown, the piercing element 24 is herein formed as a sharply pointed, elongate needle cannula 24 including the proximal end 26, a sharply pointed distal end 28 and a lumen extending therebetween. Proximal end 26 of needle cannula 24 is rigidly mounted to tip 20 of syringe barrel 12, such that the lumen through needle cannula 24 communicates with passage 22 and chamber 18 of syringe barrel 12.

An elongate cap 30 is mounted over needle cannula 24 and is releasably engaged to tip 20 of syringe barrel 12. Cap 30, which can be formed from a rigid material such as plastic, or which can be formed from a flexible material such as rubber, or from like materials or combinations known to the skilled artisan, may be configured with appropriate dimensionary sealing elements, or the like, for closing the lumen of the piercing element 24 in fluid communication with the drug and to otherwise protectively seal, engage or surround sharply pointed distal end 28 of needle cannula 24 and isolate same from the ambient environment. Thus, cap 30 prevents ambient air from communicating with the lumen through needle cannula 24.

A predetermined dose of a selected drug 32 is pre-filled into chamber 18 of syringe barrel 12, and a distal stopper 34 is slidably advanced in chamber 18 toward drug 32. As illustrated, distal stopper 34 is formed of generally cylindrical shape to conform to the generally cylindrical dimensions of syringe barrel 12. Stopper 34 includes opposed proximal and distal ends 36 and 38 and a side surface 40 extending therebetween. As the skilled artisan will appreciate, side surface 40 of distal stopper 34 may be characterized by a plurality of circumferentially extending ribs. However, other embodiments of the distal stopper may have a substantially smooth cylindrical side surface. Distal stopper 34 is preferably formed from an elastomeric material and, to effect good sliding action with the syringe barrel, laminated or coated with a material selected to exhibit low friction characteristics against the glass walls of syringe barrel 12. The material laminated or coated to the distal stopper 34 should not exhibit detrimental effects to the drug as hereinbefore mentioned and in particular, should be free of silicone-based materials such as silicone oil. For instance, the laminate or coating may be selected from the group consisting of tetrafluoroethylene resin, an ethylenetetrafluoroethylene resin, a UHMW polyethylene resin, or various carbon coatings. Thus, distal stopper 34 will be able to slide distally in chamber 18 for initial positioning adjacent drug 32 and for subsequently urging drug 32 through the lumen of needle cannula 24. However, as noted above, the low friction material laminated or coated onto distal stopper 34 has been known to risk creep over time, and hence may not be a perfect microbiological barrier for sealing drug 32 in pre-filled syringe 10.

The above-referenced potential deficiency of distal stopper 34 is overcome by a proximal stopper 42 which, as shown in FIG. 2, cooperates with distal stopper 34 to define a stopper assembly 44. Proximal stopper 42 also is of generally cylindrical configuration and includes opposed proximal and distal ends 46 and 48 respectively and a side surface 50 extending therebetween. Proximal end 46 of proximal stopper 42 includes mounting means for secure engagement with a plunger 52 of pre-filled syringe 10. As depicted herein, the mounting means on proximal stopper 42 comprises a threaded aperture formed in proximal end 46 of proximal stopper 42. A corresponding array of threads 54 is formed on the distal end of plunger 52. Other mounting means can be employed, however. Distal end 48 of proximal stopper 42 is generally planar in the embodiment depicted in FIG. 2, and can be urged into abutting engagement with proximal end 36 of distal stopper 34.

Proximal stopper 42 may be formed from rubber or other elastomeric material exhibiting microbiological sealing capabilities. Additionally, because proximal stopper 42 will be separated from drug 32 by the distal stopper 34, the proximal stopper 42 and/or syringe barrel 12 may be appropriately treated with many convenient lubricating materials, including silicone-based lubricants such as silicone oil, to facilitate sliding movement. One silicone oil applicable to the stopper 42 may entail polydimethylsiloxane. In particular, a silicone coating may be applied to at least the generally cylindrical side surface 50 of proximal stopper 42 prior to inserting proximal stopper 42 into syringe barrel 12. Alternatively, a silicone spray may be applied to the interior surface of chamber 12 after having positioned distal stopper 34 as shown in FIG. 1. With either optional embodiment, distal stopper 34 functions as a barrier that prevents contact of the lubricant such as silicone oil and from the region of proximal stopper 42 with drug 32. Proximal stopper 42 exhibits microbiological sealing, and avoids problems of leaching that might be displayed by distal stopper 34 over time in pre-filled syringe 10.

Pre-filled syringe 10 can be used substantially in the standard manner by merely removing cap 30 and urging plunger 52 distally to expel a selected amount of drug 32 through the lumen of needle cannula 24 and into a patient. The sliding distal movement of plunger 52 can be carried out easily in view of the low friction characteristics of the laminate or coating on distal stopper 34 and in view of the lubricant treatment of proximal stopper 42. However, pre-filled syringe 10 can be stored for a desirably long period of time in view of the exceptional microbiological sealing provided by elastomeric proximal stopper 42 and in view of the barrier function performed by distal stopper 34 that separates drug 32 from the lubricant such as silicone oil in proximity to proximal stopper 42.

FIG. 3 shows pre-filled syringe 10 substantially as described and illustrated above, but with an alternate stopper assembly 144. More particularly, stopper assembly 144 includes a distal stopper 134 having an open proximal end 136, a closed distal end 138 and a generally tubular sidewall 140 extending therebetween. Stopper assembly 144 further includes a proximal stopper 142 with a proximal end 146 substantially identical to proximal end 46 of proximal stopper 42 described and illustrated above. However, proximal stopper 142 further includes a distal end 148 defining an elongate projection extending into open distal end 136 of distal stopper 134 and contacting the wall defined by distal end 138. Tubular sidewall 140 of distal stopper 134 will exert adequate resilient forces against the cylindrical wall of syringe barrel 12 to function as an adequate barrier between drug 32 and distal stopper 142. However, when plunger 152 is actuated by a user, the hollow configuration of distal stopper 134, coupled with contact between distal stopper 134 and distal end projection 148 of proximal stopper 142 will cause a slight deformation and elongation of distal stopper 134. Distal stopper 134 will thus be slightly deformed away from the surface of syringe barrel 12, thereby substantially reducing forces between distal stopper 134 and syringe barrel 12 and, hence, resulting in lower required forces to urge distal stopper 134 distally for expelling drug 32 from chamber 18. In this case, it will be realized that distal stopper 134 need not necessarily be formed of a low-friction material. Hence, the alternate stopper assembly shown in FIG. 3 provides the sealing advantages referred to with respect to the FIG. 1 and 2 embodiment but with a significantly lower force required to move plunger 152 distally.

FIG. 4 shows pre-filled syringe 10 substantially as described and illustrated above, but employing a third stopper assembly 244. Stopper assembly 244 includes an axially short distal stopper 234 having a proximal end 236 defining a locking projection 237 thereon. Distal end 238 and side 240 of distal stopper 234 are structurally similar to those of distal stopper 34 shown in FIG. 1 above. Stopper assembly 244 further includes a proximal stopper 242 having a proximal end 246 substantially identical to that of proximal stopper 42 and a distal end 248 having a locking indentation 249 formed therein. In this embodiment, proximal stopper 242 is siliconized. Indentation 249 in distal end 248 of proximal stopper 242 is then lockingly engaged with projection 237 on proximal end 236 of distal stopper 234. Thereafter, the finished assembly 244 is introduced into the syringe barrel 12. Plunger 250, which can be mated to proximal stopper 242 before or after preparation of the finished assembly 244, is used to slidably advance stopper assembly 244 as previously described. The pre-assembly of proximal and distal stoppers 242 and 234 respectively can achieve certain assembly and manufacturing efficiencies. Furthermore the relatively short axial length of distal stopper 234 relative to proximal stopper 242 can result in lower sliding forces for advancing plunger 248 distally.

A fourth stopper assembly is illustrated in FIG. 5 and is identified generally by the numeral 344. Stopper assembly 344 includes a distal stopper 334 substantially identical to distal stopper 34 illustrated in FIGS. 1 and 2. Stopper assembly 344 further includes a proximal stopper in the form of a toroid and generally indicated by the numeral 342. The toroidally-shaped stopper 342 may take the form of an O-ring; however, other cross-sections such as square, ovoid, or the like are envisionable. Stopper 342 is appropriately lubricated to achieve low frictional characteristics relative to internal walls of syringe barrel 12. Stopper assembly 344 is used with a plunger 350 having a distal end 352 with an annular groove 354. As illustrated, the toroidally-shaped proximal stopper 342 is resiliently engaged in groove 354 of plunger 350. Distal end 352 of plunger 350 with the proximal stopper 342 engaged thereon can be inserted into pre-filled syringe 10 such that distal end 352 of plunger 350 engages proximal end 336 of distal stopper 334. Alternately, as seen in FIG. 5a, toroidal proximal stopper 342 and the distal stopper 334 may be disposed, affixed, or otherwise attached adjacent one another, with plunger 350 insertable therein and forming a sealing area 351 with proximal stopper 342.

FIG. 6 shows a further alternate embodiment that may be used in combination with elements of the FIG. 2 embodiment and/or the FIG. 4 embodiment. In particular, FIG. 6 illustrates a pre-filled syringe 10 substantially identical to the pre-filled syringe of FIG. 1. A distal stopper 434 substantially identical to the distal stopper in FIG. 1 is slidably inserted into open proximal end 14 of syringe barrel 12. As noted above, distal stopper 34 is formed from an elastomeric material laminated or coated with a non-silicone-based material and exhibiting desirable frictional characteristics relative to syringe barrel 12. However, as noted above, distal stopper 34 may not provide adequate sealing for long term storage of pre-filled syringe 10. Adequate sealing is, however, provided by a stopper 442 or other type of enclosure, for instance, a cap, a cover or the like, which is sealingly engaged in open proximal end 14 of syringe barrel 12. Stopper 442 is easily insertable and may be formed from a rubber or elastomer that provides good microbiological sealing capability. Immediately prior to use, stopper 442 is removed, and a plunger without a stopper or with an appropriate lubricated stopper or non-silicone laminated stopper as set forth and described above is inserted into open proximal end 14 of syringe barrel 12. The plunger inserted immediately prior to use may be plunger 52 as illustrated in FIG. 2 above or plunger 350 illustrated in FIG. 5 above. As still a further alternate, the stopper 442 may be used with the hollow proximal stopper 134 illustrated in FIG. 3 above. After removal of the stopper, the plunger 152 and proximal stopper 142 shown in FIG. 3 may then be slidably inserted into open proximal end 14 of syringe barrel 12 for expelling drug 32 from chamber 18.

It will be appreciated and understood by those skilled in the art that further and additional forms of the invention may be devised without departing from the spirit and scope of the appended claims, the invention not being limited to the specific embodiments shown.

What is claimed is:

1. A pre-fillable hypodermic syringe, comprising:
   a syringe barrel having opposed proximal and distal ends and a drug-receiving chamber therebetween, said distal end of said syringe barrel defining a passage communicating with said drug-receiving chamber; and
   a stopper assembly in said drug receiving chamber substantially adjacent a quantity of drug held in said chamber, said stopper assembly comprising a distal stopper formed from an elastomeric material having a low-friction material thereon, said low friction material substantially free of silicone-based lubricants adverse to long-term storage of the drug held in the chamber, said stopper assembly further comprising a proximal stopper formed from an elastomeric material configured and dimensioned for defining a biologically sealed interface with said syringe barrel, a lubricant being disposed at said interface for facilitating sliding movement of said proximal stopper in said syringe barrel, whereby said distal stopper isolates said drug from said proximal stopper, and whereby said proximal stopper defines a biological barrier for preventing contamination of said drug.

2. The pre-fillable syringe of claim 1 wherein said silicone-based lubricants comprising silicone oil.

3. The pre-fillable syringe of claim 1, wherein said lubricant on said proximal stopper comprises silicone oil.

4. The pre-fillable syringe of claim 1, wherein said lubricant disposed at the interface is coated onto said proximal stopper.

5. The pre-fillable syringe of claim 1, wherein said lubricant disposed at the interface is laminated onto said proximal stopper.

6. The pre-fillable syringe of claim 1, wherein said lubricant at said interface is coated onto portions of said syringe barrel between said distal stopper and said proximal end of said syringe barrel.

7. The pre-fillable syringe of claim 1, wherein said proximal and distal stoppers are in abutting engagement with one another.

8. The pre-fillable syringe of claim 7, wherein said proximal stopper and said distal stopper are lockably engaged with one another.

9. The pre-fillable syringe of claim 1, wherein said distal stopper includes a distal wall, a generally tubular side wall projecting proximally from said distal wall and a substantially open proximal end, said proximal stopper including a distal end defining a projection extending into said open proximal end of said distal stopper and engaging said distal wall of said distal stopper.

10. The pre-fillable syringe of claim 1, further comprising a rigid plunger having opposed proximal and distal ends, said proximal end of said plunger projecting from said proximal end of said syringe barrel, said distal end of said plunger being disposed within said syringe barrel and disposed at least with said proximal stopper of said stopper assembly.

11. The pre-fillable syringe of claim 10, wherein said proximal stopper comprises a toroid-shaped stopper mounted to said distal end of said plunger.

12. The pre-fillable syringe of claim 10, wherein said proximal stopper comprises a toroid-shaped stopper mounted to the distal stopper.

13. The pre-fillable syringe of claim 1, wherein said proximal stopper is spaced proximally from said distal stopper.

14. The pre-fillable syringe of claim 1, wherein said proximal stopper is releasably engaged adjacent said proximal end of said syringe barrel.

15. The pre-fillable syringe of claim 1, wherein said low friction material is laminated onto the distal stopper, the low friction material selected from the group consisting of tetrafluoroethylene resin, an ethylenetetrafluoroethylene resin or a UHMW polyethylene resin.

16. The pre-fillable syringe of claim 1, wherein said low friction material is coated onto said distal stopper.

17. The pre-fillable syringe of claim 1, further comprising sealing means for sealing said passage communicating with said drug receiving chamber.

18. The pre-fillable syringe of claim 1, further comprising a drug disposed in said drug receiving chamber and extending from said distal end of said syringe barrel to a location intermediate said proximal and distal ends.

19. A stopper assembly for a pre-filled syringe, said syringe including a syringe barrel having opposed proximal and distal ends and a drug-receiving chamber therein for receiving a drug in portions of said chamber adjacent said distal end, said stopper assembly comprising a distal stopper comprising an elastomeric material laminated with a silicone-free low friction material, said distal stopper being dimensioned and configured for disposition within said drug-receiving chamber in fluid-tight sliding engagement with said syringe barrel, a proximal stopper having opposed proximal and distal ends disposed such that said distal end of said proximal stopper is adjacent said distal stopper, said proximal stopper being formed from an elastomeric material and being dimensioned for disposition in said fluid receiving chamber in sliding biologically sealing engagement with said syringe barrel, said proximal stopper being coated with a silicone lubricant for facilitating sliding movement of said stopper assembly in said syringe barrel.

20. The stopper assembly of claim 19, wherein said proximal and distal stoppers are lockingly engaged with one another.

21. The stopper assembly of claim 19, wherein said distal stopper includes a distal end wall, a tubular side wall and an open proximal end, said distal end of said proximal stopper defining a projection extending into said open proximal end of said distal stopper and engaging said distal wall of said distal stopper.

22. The stopper assembly of claim 19, wherein said proximal end of said proximal stopper defines attachment means for attaching said proximal stopper to a plunger of said pre-filled syringe.

23. The stopper assembly of claim 19, wherein said low friction material laminated onto said distal stopper is selected from the group consisting of tetrafluoroethylene resin, an ethylenetetrafluoroethylene resin or a UHMW polyethylene resin.

24. The stopper assembly of claim 1, wherein the low friction material disposed onto said distal stopper comprises a carbon material.

25. The stopper assembly of claim 19, wherein the low-friction material laminated onto said distal stopper comprises a carbon material.

* * * * *